(12) United States Patent
Burns et al.

(10) Patent No.: US 6,241,964 B1
(45) Date of Patent: Jun. 5, 2001

(54) F-18 RADIOLABELED NEUROKININ-1 RECEPTOR ANTAGONISTS

(75) Inventors: H. Donald Burns, Harleysville; Terence G. Hamill, Lansdale; Raymond E. Gibson, Holland, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/407,822

(22) Filed: Sep. 28, 1999

Related U.S. Application Data

(60) Provisional application No. 60/102,334, filed on Sep. 29, 1998.

(51) Int. Cl.[7] .................. A61K 51/00; C07D 401/00; C07D 211/56; G01N 33/53; G01N 33/534
(52) U.S. Cl. ................. 424/1.89; 546/210; 546/223; 435/7.1; 436/804
(58) Field of Search .................. 424/1.89, 1.85, 424/1.81, 1.65, 1.41, 1.45; 435/7.1, 122; 546/210, 223, 244; 514/326, 329, 381; 548/250, 252, 254; 436/804, 501, 504

(56) References Cited

U.S. PATENT DOCUMENTS 5,719,156 * 2/1998 Shue et al. ............... 514/255

FOREIGN PATENT DOCUMENTS

WO 96/21661  7/1996 (WO).
WO 98/57909  12/1998 (WO).

OTHER PUBLICATIONS

Mishani, E. et al., Synthesis and evaluation of a fluorine–18 labeled NK–1 antagonist, Jour. of Labeled Compounds and Radiopharmaceuticals, vol. 40, pp. 653–655, Dec. 1997.*

Casdata–CA 125:4529, Tomiyoshi, et al, "positron emission tomography for evaluation of dopaminergic function using a neurotransmitter analog L–18F–m–tyrosin in monkey brain" Bioimages vol. 4. No. 1, pp. 1–7 (1996).

Casdata–CA 126:118149, Oosaki, et al, "method for producing fluorine radioisotope–Ibeled organic compound [18F]–2–fluoro–2–deoxy–d–glucose" (1996) JP 08325169, see entire abstract.

Casdata–CA 126:18876, Giblin et al, "Preparation of 3–(tetrazolylbenzylamino)–2–phenylpiperidines as neurokinin antagonists" (1996) WO 96/29326, see abstract and RN180574–25–8.

Greene, T.W., Protective groups in organic synthesis, John Wiley & sons, p. 232 (1982).

* cited by examiner

*Primary Examiner*—Michael G. Hartley
(74) *Attorney, Agent, or Firm*—J. Eric Thies; David L. Rose

(57) ABSTRACT

The present invention is directed to radiolabeled neurokinin-1 receptor antagonists which are useful for the labeling and diagnostic imaging of neurokinin-1 receptors in mammals.

14 Claims, No Drawings

F-18 RADIOLABELED NEUROKININ-1 RECEPTOR ANTAGONISTS

This application claims the benefit of U.S Provisional Application No. 60/102,334, filed Sep. 29, 1998.

BACKGROUND OF THE INVENTION

Noninvasive, nuclear imaging techniques can be used to obtain basic and diagnostic information about the physiology and biochemistry of a variety of living subjects including experimental animals, normal humans and patients. These techniques rely on the use of sophisticated imaging instrumentation which is capable of detecting radiation emitted from radiotracers administered to such living subjects. The information obtained can be reconstructed to provide planar and tomographic images which reveal distribution of the radiotracer as a function of time. Use of appropriately designed radiotracers can result in images which contain information on the structure, function and most importantly, the physiology and biochemistry of the subject. Much of this information cannot be obtained by other means. The radiotracers used in these studies are designed to have defined behaviors in vivo which permit the determination of specific information concerning the physiology or biochemistry of the the subject or the effects that various diseases or drugs have on the physiology or biochemistry of the subject. Currently, radiotracers are available for obtaining useful information concerning such things as cardiac function, myocardial blood flow, lung perfusion, liver function, brain blood flow, regional brain glucose and oxygen metabolism.

Compounds can be labeled with either positron or gamma emitting radionuclides. For imaging, the most commonly used positron emitting (PET) radionuclides are $^{11}C$, $^{18}F$, $^{15}O$ and $^{13}N$, all of which are accelerator produced, and have half lifes of 20, 110, 2 and 10 min. respectively. Since the half-lives of these radionuclides are so short, it is only feasible to use them at institutions which have an accelerator on site for their production, thus limiting their use. Several gamma emitting radiotracers are available which can be used by essentially any hospital in the U.S. and in most hospitals worldwide. The most widely used of these are $^{18}F$, $^{99m}Tc$, $^{201}Tl$ and $^{123}I$.

In the past decade, one of the most active areas of nuclear medicine research has been the development of receptor imaging radiotracers. These tracers bind with high affinity and specificity to selective hormone receptors and neuroreceptors. Successful examples include radiotracers for imaging the following receptor systems: estrogen, muscarinic, dopamine D1 and D2, and opiate.

The neuropeptide receptors for substance P (neurokinin-1; NK-1) are widely distributed throughout the mammalian nervous system (especially brain and spinal ganglia), the circulatory system and peripheral tissues (especially the duodenum and jejunum) and are involved in regulating a number of diverse biological processes. This includes sensory perception of olfaction, vision, audition and pain, movement control, gastric motility, vasodilation, salivation, and micturition (B. Pernow, *Pharmacol. Rev.*, 1983, 35, 85–141). The NK-1 and NK-2 receptor subtypes are implicated in synaptic transmission (Laneuville et al., *Life Sci.*, 42: 1295–1305 (1988)). The receptor for substance P is a member of the superfamily of G protein-coupled receptors. This superfamily is an extremely diverse group of receptors in terms of activating ligands and biological functions.

Substance P (also called "SP" herein) is a naturally occurring undecapeptide belonging to the tachykinin family of peptides, the latter being so-named because of their prompt contractile action on extravascular smooth muscle tissue. In addition to SP the known mammalian tachykinins include neurokinin A and neurokinin B. The current nonmenclature designates the receptors for SP, neurokinin A, and neurokinin B as NK-1, NK-2, and NK-3, respectively. Neurokinin-1 (NK-1; substance P) receptor antagonists are being developed for the treatment of a number of physiological disorders associated with an excess or imbalance of tachykinins, and in particular substance P. Substance P has been implicated in gastrointestinal (GI) disorders and diseases of the GI tract, such as emesis [*Trends Pharmacol. Sci.*, 9, 334–341 (1988), F. D. Tatersall, et al., *Eur. J. Pharmacol.*, 250, R5–R6 (1993)], and in psychiatric disorders, such as depression (Kramer, et al., *Science*, 281, 1640–1645 (Sep. 11, 1998). The compound [2-fluoromethoxy-5-(5-trifluoromethyl-tetrazol-1-yl)-benzyl]-([2S,3S]-2-phenyl-piperidin-3-yl)-amine is disclosed in PCT Patent Publication WO 96/21661 as a tachykinin antagonist.

PET (Positron Emission Tomography) radiotracers and imaging technology may provide a powerful method for clinical evaluation and dose selection of neurokinin-1 receptor antagonists. Using a fluorine-18 or carbon-11 labeled radiotracer that provides a neurokinin-1 receptor-specific image in the brain and other tissues, the dose required to saturate neurokinin-1 receptors can be determined by the blockade of the PET radiotracer image in humans. The rationale for this approach is as follows: efficacy of a neurokinin-1 receptor antagonist is a consequence of the extent of receptor inhibition, which in turn is a function of the degree of drug-receptor occupancy.

It is, therefore, an object of this invention to develop radiolabeled neurokinin-1 receptor antagonists that would be useful not only in traditional exploratory and diagnostic imaging applications, but would also be useful in assays, both in vitro and in vivo, for labeling the neurokinin-1 receptor and for competing with unlabeled neurokinin-1 receptor antagonists and agonists. It is a further object of this invention to develop novel assays which comprise such radiolabeled compounds.

SUMMARY OF THE INVENTION

The present invention is directed to certain radiolabeled neurokinin-1 receptor antagonists. The present invention is further concerned with methods for the use of such radiolabeled neurokinin-1 receptor antagonists for the labeling and diagnostic imaging of neurokinin-1 receptors in mammals.

DETAILED DESCRIPTION OF THE INVENTION

The present invention is directed to certain radiolabeled neurokinin-1 receptor antagonists. In particular, the present invention is directed to a compound of the formula:

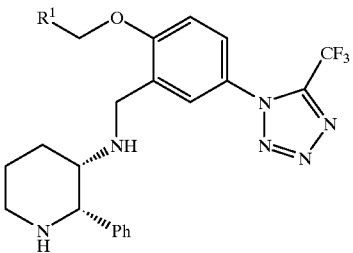

wherein:

R₁ is a radionuclide selected from the group consisting of: $^3$H, $^{11}$C, $^{18}$F, $^{125}$I, $^{82}$Br, $^{123}$I, $^{131}$I, $^{75}$Br, $^{15}$O, $^{13}$N, $^{211}$At and $^{77}$Br;

and pharmaceutically acceptable salts thereof.

In a preferred embodiment of the present invention R₁ is $^{11}$C or $^{18}$F.

In a more preferred embodiment of the present invention R₁ is $^{18}$F.

In an even more preferred embodiment the present invention is directed to the compound

[$^{18}$F][2-fluoromethoxy-5-(5-trifluoromethyl-tetrazol-1-yl)-benzy]-([2S,3S]-2-phenyl-piperidin-3-yl)-amine which may be depicted as:

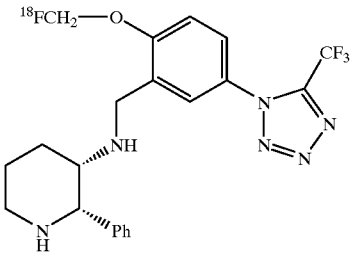

The present invention is also directed to a radiopharmaceutical composition which comprises a compound of the present invention and at least one pharmaceutically acceptable carrier or excipient.

The present invention is also directed to a method for labeling neurokinin-1 receptors in a mammal which comprises administering to a mammal in need of such labeling an effective amount of the radiolabeled compound of the present invention.

The present invention is also directed to a method for diagnostic imaging of neurokinin-1 receptors in a mammal which comprises administering to a mammal in need of such diagnostic imaging an effective amount of the radiolabeled compound of the present invention.

The present invention is also directed to a method for diagnostic imaging of tissues bearing neurokinin-1 receptors in a mammal which comprises administering to a mammal in need of such diagnostic imaging an effective amount of the radiolabeled compound of the present invention.

The present invention is also directed to a method for diagnostic imaging of substance P binding sites in tissues of a mammalian species which comprises administering to the mammalian species in need of such diagnostic imaging an effective amount of the radiolabeled compound of the present invention.

The present invention is also directed to a method for diagnostic imaging of the brain in a mammal which comprises administering to a mammal in need of such diagnostic imaging an effective amount of the radiolabeled compound of the present invention.

The present invention is further directed to a method for the detection or quantification of neurokinin-1 receptors in mammalian tissue which comprises administering to a mammal in which such quantification is desired an effective amount of the radiolabeled compound of the present invention.

In a preferred embodiment of the methods of the present invention, the mammal is a human.

The present invention is further directed to a process for the preparation of [$^{18}$F][2-fluoromethoxy-5-(5-trifluoromethyl-tetrazol-1-yl)-benzyl]-([2S,3S]-2-phenyl-piperidin-3-yl)-amine which comprises:

contacting ((2S,3S)-1-t-butoxycarbonyl-2-phenyl-3-[2-hydroxy-5-(5'-trifluoro-methyltetrazo-1-yl)phenylmethylene-amino]piperidine with an alkylating agent selected from [$^{18}$F]iodofluoromethane and [$^{18}$F]bromofluoromethane in the presence of a weak base, such as cesium carbonate, in an inert solvent, such as dimethylformamide, at a temperature between room temperature and solvent reflux temperature, preferably about 70–80° C.; and contacting the resultant product with a strong acid, such as trifluoracetic acid.

Suitable radionuclides that may be incorporated in the instant compounds include $^3$H (also written as T), $^{11}$C, $^{18}$F, $^{125}$I, $^{82}$Br, $^{123}$I, $^{131}$I, $^{75}$Br, $^{15}$O, $^{13}$N, $^{211}$At or $^{77}$Br. The radionuclide that is incorporated in the instant radiolabeled compounds will depend on the specific analytical or pharmaceutical application of that radiolabeled compound. Thus, for in vitro labeling of neurokinin receptors and competition assays, compounds that incorporate $^3$H, $^{125}$I or $^{82}$Br will generally be most useful. For diagnostic imaging agents, compounds that incorporate a radionuclide selected from $^{11}$C, $^{18}$F, $^{123}$I, $^{131}$I, $^{75}$Br, $^{76}$Br or $^{77}$Br are preferred. In certain applications incorporation of a chelating radionuclide such as Tc$^{99m}$ may also be useful. In the present invention, $^{18}$F is particularly preferred over $^{11}$C because with the longer half-life of $^{18}$F, imaging can be carried out long enough to allow a more specific signal to develop and improved conditions for receptor quantification studies.

Radiolabeled neurokinin-1 receptor antagonists, when labeled with the appropriate radionuclide, are potentially useful for diagnostic imaging, basic research, and radiotherapeutic applications. Specific examples of possible diagnostic imaging and radiotherapeutic applications, include determining the location, the relative activity and/or the abundance of neurokinin-1 receptors, radioimmunoassay of neurokinin-1 receptor antagonists, and autoradiography to determine the distribution of neurokinin-1 receptors in a mammal or an organ or tissue sample thereof.

In particular, the instant radiolabeled neurokinin-1 receptor antagonists when labeled with the positron emitting radionuclide, F-18, are useful for positron emission tomographic (PET) imaging of neurokinin-1 receptors in the brain of living humans and experimental animals. This radiolabeled neurokinin-1 receptor antagonists may be used as research tools to study the interaction of unlabeled neurokinin-1 antagonist with neurokinin-1 receptors in vivo via competition between the labeled drug and the radiolabeled compound for binding to the receptor. This type of study is useful for determining the relationship between neurokinin-1 receptor occupancy and dose of unlabeled neurokinin-1 receptor antagonist, as well as for studying the duration of blockade of the receptor by various doses of the unlabeled neurokinin-1 receptor antagonist. As a clinical tool, the radiolabeled neurokinin-1 receptor antagonists may be used to help define a clinically efficacious dose of a neurokinin-1 receptor antagonist. In animal experiments, the radiolabeled neurokinin-1 receptor antagonists can be used to provide information that is useful for choosing between potential drug candidate for selection for clinical development. The radiolabeled neurokinin-1 receptor antagonists may also be used to study the regional distribution and concentration of neurokinin-1 receptors in the living human brain, as well as the brain of living experimental animals and in tissue samples. The radiolabeled neurokinin-1 receptor antagonists may also be used to study disease or pharmacologically related changes in neurokinin-1 receptor concentrations.

For example, positron emission tomography (PET) tracer such as the present radiolabeled neurokinin-1 receptor antagonists which can be used with currently available PET technology to obtain the following information: relationship between level of receptor occupancy by candidate neurokinin-1 antagonist and clinical efficacy in patients; dose selection for clinical trials of neurokinin-1 antagonists prior to initiation of long term clinical studies; comparative potencies of structurally novel neurokinin-1 antagonists; investigating the influence of neurokinin-1 antagonists on in vivo receptor affinity and density during the treatment of clinical targets with neurokinin-1 receptor antagonists and other agents; changes in the density and distribution of neurokinin-1 receptors during e.g. psychiatric diseases in their active stages, during effective and ineffective treatment and during remission; and changes in neurokinin-1 receptor expression and distribution in CNS disorders (e.g. depression, head injury and Parkinson's disease).

For the use of the instant compounds as exploratory or diagnostic imaging agents the radiolabeled compounds may be administered to mammals, preferably humans, in a pharmaceutical composition, either alone or, preferably, in combination with pharmaceutically acceptable carriers or diluents, optionally with known adjuvants, such as alum, in a pharmaceutical composition, according to standard pharmaceutical practice. Such compositions can be administered orally or parenterally, including the intravenous, intramuscular, intraperitoneal, subcutaneous, rectal and topical routes of administration. Preferably, administration is intravenous.

Radiotracers labeled with short-lived, positron emitting radionuclides are almost always administered via intravenous injection within less than one hour of their synthesis. This is necessary because of the short half-life of the radionuclides involved (20 and 110 minutes for C-11 and F-18 respectively).

The pharmaceutical compositions of this invention may be used in the form of a pharmaceutical preparation, for example, in solid, semisolid or liquid form, which contains one or more of the compound of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solution, suitably flavoured syrups, aqueous or oil suspensions, and emulsions with acceptable oils such as cottonseed oil, sesame oil, coconut oil or peanut oil, or with a solubilizing or emulsifying agent suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

A minimum dosage level for the unlabeled neurokinin-1 receptor antagonist is about 1 mg per day, preferably about 5 mg per day and especially about 10 mg per day. A maximum dosage level for the neurokinin-1 receptor antagonist is about 1500 mg per day, preferably about 1000 mg per day and especially about 500 mg per day. It will be appreciated that the amount of the neurokinin-1 receptor antagonist required for use in the present invention will vary not only with the particular compounds or compositions selected but also with the route of administration, the nature of the condition being treated or studied, and the age and condition of the patient, and will ultimately be at the discretion of the patient's physician or pharmacist.

When a radiolabeled neurokinin-1 receptor antagonist according to this invention is administered into a human subject, the amount required for diagnostic imaging will normally be determined by the prescribing physician with the dosage generally varying according to the age, weight, and response of the individual patient, as well as the quantity of emission from the radionuclide. However, in most instances, an effective amount will be the amount of compound sufficient to produce emissions in the range of from about 1–5 mCi.

In one exemplary application, administration occurs in an amount of radiolabeled compound of between about 0.005 µg/kg of body weight to about 50 µg/kg of body weight per day, preferably of between 0.02 µg/kg of body weight to about 3 µg/kg of body weight. A particular analytical dosage that comprises the instant composition includes from about 0.5 µg to about 100 µg of a labeled neurokinin-1 receptor antagonist. Preferably, the dosage comprises from about 1 µg to about 50 µg of a radiolabeled neurokinin-1 receptor antagonist.

The following illustrative procedure may be utilized when performing PET imaging studies on patients in the clinic. The patient is premedicated with unlabeled neurokinin-1 receptor antagonist (at doses 300, 100, or 30 mg/day) for 2 weeks prior to the day of the experiment and is fasted for at least 12 hours allowing water intake ad libitum. A 20 G two inch venous catheter is inserted into the contralateral ulnar vein for radiotracer administration.

The patient is positioned in the PET camera and a tracer dose of $[^{15}O]H_2O$ administered via i.v. catheter. The image thus obtained is used to insure that the patient is positioned correctly to include the brain or other areas of interest. Subsequently the $[^{18}F]$neurokinin-1 receptor antagonist (<20 mCi) is administered via i.v. catheter. Following the acquisition of the total radiotracer image, an infusion is begun of the neurokinin-1 receptor antagonist which is being clinically evaluated at one of three dose rates (0.1, 1 or 10 mpk/day). After infusion for 2.5 hrs, the $[^{18}F]$ neurokinin-1 receptor antagonist is again injected via the catheter. Images are again acquired for up to 90 min. Within ten minutes of the injection of radiotracer and at the end of the imaging session, 1 ml blood samples are obtained for determining the plasma concentration of the clinical candidate.

For determining the distribution of radiotracer, regions of interest (ROIs) are drawn on the reconstructed image including, e.g. the brain and the central nervous system. These regions are used to generate time activity curves obtained in the absence of receptor antagonist or in the presence of the clinical candidate at the various infusion doses examined. Data are expressed as radioactivity per unit time per unit volume (µCi/cc/mCi injected dose). Inhibition curves are generated from the data obtained in a region of interest obtained starting at 70 minutes post-injection of radiotracer. At this time, clearance of non-specific binding has reached steady state.

The $ID_{50}$ values are obtained by curve fitting the dose-rate/inhibition curves with equation iii:

$$B=A_0-A_0*I/(ID_{50}+I)+NS \qquad (iii)$$

where B is the %-Dose/g of radiotracer in tissues for each dose of clinical candidate, $A_0$ is the specifically bound radiotracer in a tissue in the absence of a neurokinin-1 receptor antagonist, I is the injected dose of antagonist, $ID_{50}$ is the dose of compound which inhibits 50% of specific radiotracer binding to a neurokinin receptor, and NS is the amount of non-specifically bond radiotracer.

Gamma Camera Imaging

Two rats are anesthetized (ketamine/ace-promazine), positioned on the camera head, and their tail veins canulated for ease of injection. One rat is preinjected with an unlabeled neurokinin-1 receptor antagonist (10% EtOH/27% PEG/63% $H_2O$) 30 min. prior to injection of radiotracer to demonstrate non-specific binding. 150 uCi/rat of an $^{18}F$ labeled neurokinin-1 receptor antagonist is injected via its tail vein, and the catheters flushed with several mls of normal saline. Acquisition of images is started as the radiotracer was injected. Sixty, one minute images are acquired and the rats are subsequently euthanized with sodium pentobarbital. Regions of interest (ROIs) are drawn on the first image which includes the brain, then used to analyze the count rates in subsequent images. ROIs are defined to remain fairly clear during the course of the study, and are assumed to be representative of the entire organ. Count-rates are converted to %-dose/ROI by dividing the count-rate in the ROI by that of the whole rat, which is then multiplied by 100.

PET Imaging in Dogs

Female beagle dogs weighing 7.7–14.6 kg (11.0±2.3 kg) are premedicated with unlabeled neurokinin-1 receptor antagonist (at doses 300, 100, or 30 mg/day) for 2 weeks prior to the day of the experiment and are fasted for at least 12 hours allowing water intake ad libitum. A 20 G two inch venous catheter is placed into the right front leg ulnar vein through which anesthesia is introduced by sodium pentobarbital 25–30 mg/kg in 3–4 ml and maintained with additional pentobarbital at an average dose of 3 mg/kg/hr. Another catheter is inserted into the contralateral ulnar vein for radiotracer administration.

Oxygen saturation of circulating blood is measured with a pulse oximeter (Nellcor Inc., Hayward, Calif.) placed on the tongue of the animal. Circulatory volume is maintained by intravenous infusion of isotonic saline. A 22 G cannula is inserted into the anterior tibial or distal femoral artery for continuous pressure monitoring (Spacelabs™, model 90603A). EKG, heart rate, and core temperature are monitored continuously. In particular, EKG is observed for ST segment changes and arrhythmias.

The animal is positioned in the PET camera and a tracer dose of $[15O]H_2O$ administered via i.v. catheter. The image thus obtained is used to insure that the dog is positioned correctly to include the brain and other areas of interest. Subsequently $[^{18}F]$-neurokinin-1 receptor antagonist (<20 mCi) is administered via i.v. catheter. Following the acquisition of the total radiotracer image, an infusion is begun of the unlabeled neurokinin-1 receptor antagonist at one of three dose rates (0.1, 1 or 10 mpk/day). After infusion for 2.5 hrs, $[^{18}F]$-neurokinin-1 receptor antagonist is again injected via the catheter. Images are again acquired for up to 90 min. Within ten minutes of the injection of radiotracer and at the end of the imaging session, 1 ml blood samples are obtained for determining the plasma concentration of test compound. In one imaging session, a dose of 10 mpk another neurokinin-1 receptor antagonist is infused over 5 minutes. This dose has been determined to completely block radiotracer binding and thus is used to determine the maximum receptor-specific signal obtained with the PET radiotracer. At the conclusion of the study, animals are recovered and returned to animal housing.

For uninhibited distribution of radiotracer, regions of interest (ROIs) are drawn on the reconstructed image including the brain. These regions are used to generate time activity curves obtained in the absence of test compound or in the presence of test compound at the various infusion doses examined. Data are expressed as radioactivity per unit time per unit volume (µCi/cc/mCi injected dose). Inhibition curves are generated from the data obtained in a region of interest obtained starting at 70 min. post-injection of radiotracer. By this time, clearance of non-specific binding will have reached steady state. The $ID_{50}$ are were obtained by curve fitting the dose-rate/inhibition curves with equation iii, hereinabove.

Neurokinin-1 receptor antagonists which incorporate a radionuclide may be prepared by first synthesizing an unlabeled compound that optionally incorporates a iodo or bromo moiety and then exchanging a hydrogen or halogen moiety with an appropriate radionuclide using techniques well known in the art. Alternately, a radiolabeled neurokinin-1 receptor antagonist may be prepared by alkylation with a radiolabeled alkylating agent. Syntheses of unlabeled neurokinin-1 receptor antagonist have been generally described in the patent publications cited hereinabove. Syntheses of particular neurokinin-1 receptor antagonists is described below.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

In particular, amino moieties may be protected by, for example, the formation of alkoxycarbonyl derivatives, e.g. tert-butoxycarbonyl and trichloroethoxycarbonyl, or benzyl, trityl or benzyloxycarbonyl derivatives. Subsequent removal of the protecting group is achieved by conventional procedures thus, for example, tert-butoxycarbonyl, benzyl or benzyloxycarbonyl groups may be removed by hydrogenolysis in the presence of a catalyst e.g. palladium; a trichloroethoxycarbonyl group may be removed with zinc dust; and a trityl group may be removed under acidic conditions using standard procedures.

Where hydroxyl groups require protection, this may be effected by the formation of esters or trialkylsilyl, tetrahydropyran or benzyl ethers. Such derivatives may be deprotected by standard procedures thus, for example, a tetrahydropyran ether derivative may be deprotected using hydrochloric acid in methanol.

In some cases the order of carrying out the following reaction schemes may be varied to facilitate the reaction or to avoid unwanted reaction products.

The following examples are provided for the purpose of further illustration only and are not intended to be limitations on the disclosed invention.

EXAMPLE 1

(2S,3S)-(−)-3-Amino-2-phenylpiperidine

The title compound is prepared essentially as described below.

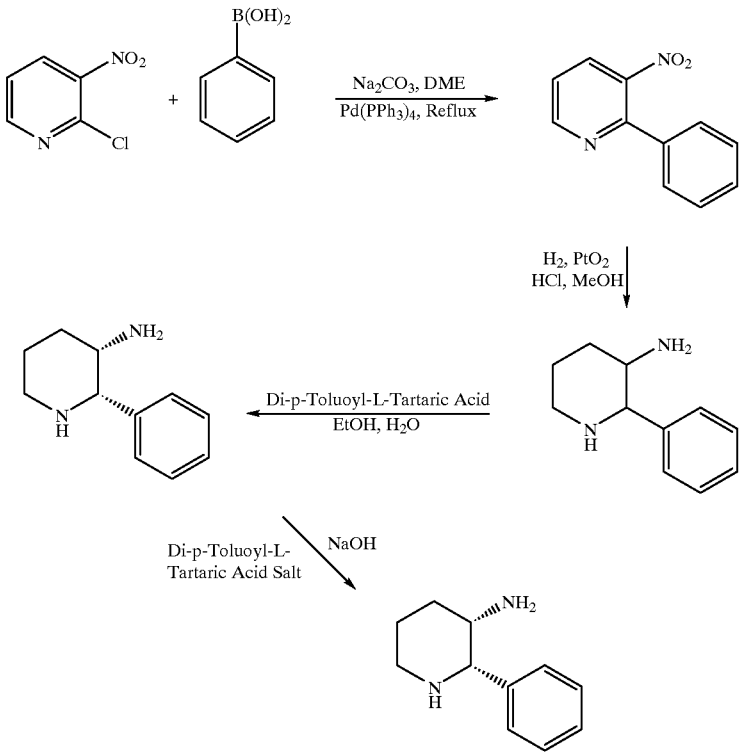

Step 1: 2-Phenyl-3-nitropyridine

A 5 L round bottom flask fitted with a condenser, mechanical stirrer and a nitrogen inlet was charged with 152.3 g (0.96 mol) of 2-chloro-3-nitropyridine and 1.65 L of 1,2-dimethoxyethane. The solution was degassed by bubbling nitrogen through the solution for 10 min and 56.7 g (0.49 mol, 0.05 equiv) of tetrakis(triphenylphosphine)-palladium (0) was added. The mixture was degassed for an additional 45 min during which time the catalyst dissolved leaving a clear dark red solution. A degassed solution of 180.3 g (1.48 mol, 1.54 equiv) of phenylboronic acid in 800 mL of absolute ethanol was added followed by 1.65 L of degassed 2M aqueous sodium carbonate solution. The cloudy mixture was heated to reflux, and refluxed for 1.5 h. While at reflux a yellow suspension formed. The suspension was cooled to ambient temperature, diluted with 1 L of ethyl acetate, and filtered through Celite®. The cake was washed with 2 L of ethyl acetate and the filtrate washed with water (2×3 L), saturated sodium bicarbonate solution (1×3 L), and saturated sodium chloride solution (1×3 L). The organic layer was dried with magnesium sulfate, filtered and the filtrate concentrated. The residue was dissolved in 1.5 L of ether, washed with 2.5N NaOH (2×500 mL) and brine (500 mL). The solution was dried with magnesium sulfate, filtered through 400 g of silica and the cake washed with additional ethyl acetate. The filtrate was concentrated to an oil which was chromatographed [5 kg Silica Gel 60, 70–230 mesh, hexanes/ethyl acetate 80:20 (12 L), 75:25 (8 L), 70:30 (11 L) and 60:40 (7 L)]. The product fractions were concentrated yielding 188.0 g (97% yield) of the title compound 2-phenyl-3-nitropyridine, as a pale yellow oil: $^1$H NMR (CDCl$_3$) δ 7.39–7.49 (m, 4H), 753–7.95 (m, 2H), 8.12 (m, 1H) 8.84 (m, 1H). MS (EI) m/z 200. Anal. Calcd for $C_{11}H_8N_2O_4$: C, 66.00; H, 4.03; N, 13.99. Found: C, 66.19; H, 4.09; N, 13.98.

Step 2: cis-2-Phenyl-3-aminopiperidine

A solution of 30 g (0.15 mol) of 2-phenyl-3-nitropyridine in 190 mL of methanol was hydrogenated using 5 g of platinum oxide with an initial pressure of 45 psi hydrogen. After 2 h, 50 mL of conc HCl was added, the vessel repressurized to 45 psi, and the reduction continued for an additional 6.25 h. The reaction was diluted with water (100 mL) and filtered. Three reactions were combined at this point and the combined cake washed with methanol (200 mL), water (100 mL), methanol (200 mL), water (100 mL), and methanol (200 mL). The filtrate was concentrated, the residue treated with 500 mL of 5N NaOH and extracted with ether (3×1 L) and methylene chloride (2×1 L). The combined extracts were dried with sodium sulfate, filtered and the filtrate concentrated to afford 80.9 g of a pale yellow oil. Chromatography (5 kg Silica Gel 60, 70–230 mesh, methylene chloride/methanol/ammonium hydroxide 92.5:7.5:0.75) afforded 62 g (78% yield) of cis-2-phenyl-3-aminopiperidine as a pale yellow oil: $^1$H NMR (CDCl$_3$) δ 1.35–1.55 (m, 4H), 1.65–1.98 (m, 3H), 2.75 (m, 1H), 2.95 (m, 1H), 3.17 (m, 1H), 3.8 (bs, 1H), 7.19–7.37 (m, 5H). MS (EI) m/z 176.

Step 3: [2S]-Phenyl-piperidin-[3S]-yl-amine[2R,3R]-bis(4-methyl-benzyloxy)-succinate To a solution of 41 g (0.23 mol) of cis-2-phenyl-3-aminopiperidine in ethanol (3.25 L) and water (440 mL) at 60° C. was added 88 g (0.23 mol) of di-p-toluoyl-L-tartaric acid. The acid dissolved quickly leaving a clear pale yellow solution. After a few minutes a suspension formed. Heating was continued for 20 min. The suspension was allowed to cool, with stirring, to ambient temperature overnight. The product was collected by filtration, washed with ethanol (200 mL) and ether (200 mL) and air dried affording 60.0 g of the title compound (86% of theory). [α]$^{20}_D$=–54° (C=0.5, MeOH). HPLC analysis (Chiracel OD-R, 4.6×250 mm column, 0.5 mL/min 55:45 0.1% TFA-water/acetonitile 35° C., λ 245) showed the material had a very high optical purity with no detectable amount of the other enantiomer: Calcd for $C_{31}H_{34}N_2O_8$:H$_2$O: C, 64.13; H, 6.25; N, 4.83. Found: C, 6.22; H, 6.33; N, 4.75. KF=3.48% (theory 3.1%).

Step 4: (2S,3S)-(–)-3-amino-2-phenylpiperidine

[2S]-Phenyl-piperidin-[3S]-yl-amine[2R,3R]-bis(4-methyl-benzyloxy)-succinate (5 g, 8.33 mmol)) was partitioned between 100 mL of methylene chloride and 25 mL of 1N NaOH. The aqueous was re-extracted with 50 mL of methylene chloride and the combined organic layer dried with sodium sulfate, filtered and concentrated.

EXAMPLE 2

(2S,3S)-1-t-Butoxycarbonyl-2-phenyl-3-[2-hydroxy-5-(5'-trifluoromethyltetrazo-1-yl)phenylmethyleneamino]piperidine The title compound is prepared essentially as outlined below.

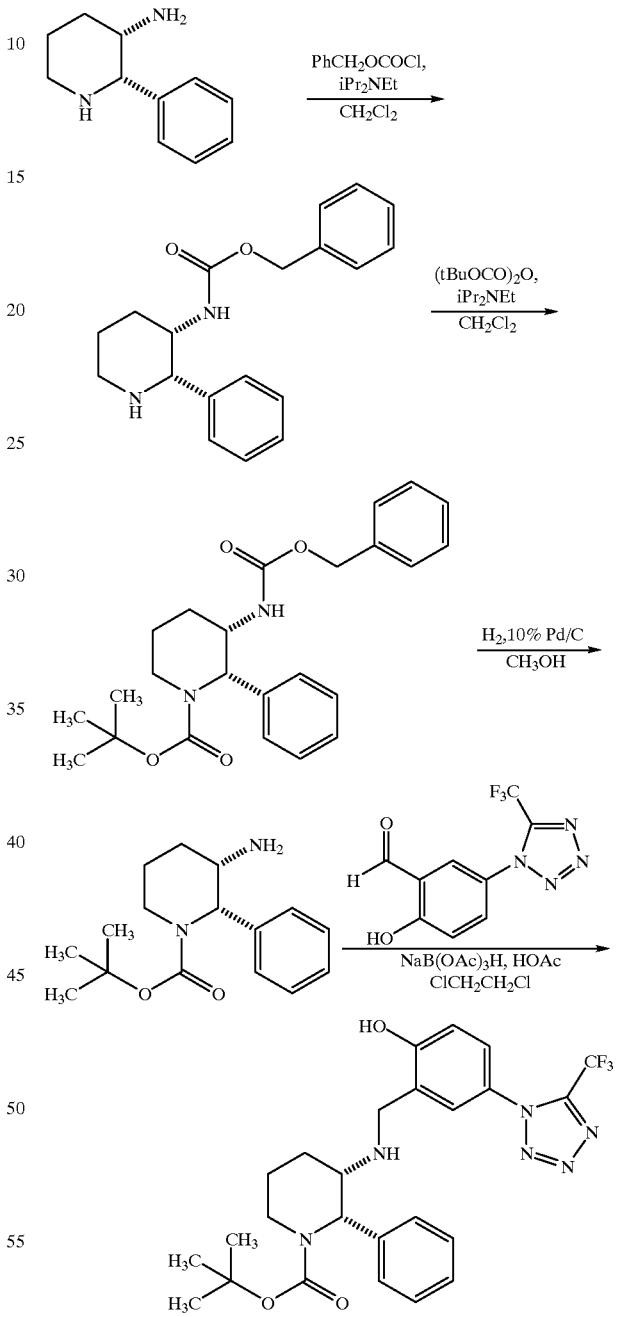

Step 1: (2S,3S)-3-Benzyloxycarbonylamino-2-phenylpiperidine

To a solution of (2S,3S)-(–)-3-amino-2-phenylpiperidine (152 mg, 0.86 mmole) (L-tartaric acid salt, [a]$_D$=–57.1 (EtOH, c=0.1138)) in methylene chloride (10 mL) at room temperature was added benzyl chloroformate (0.123 mL, 0.86 mmole) and diisopropylethylamine (0.45 mL, 2.58 mmole). The reaction was stirred for 16 hours and was then diluted with methylene chloride and quenched by addition of water. The mixture was separated and the aqueous was reextracted with 2 additional aliquots of methylene chloride. The organic layers were successively washed with a portion of brine, dried over sodium sulfate, combined and evaporated. The residue was purified by flash chromatography (5% methanol in methylene chloride) to afford 214 mg (80%) of the title compound. NMR (CDCl$_3$): δ 1.55 (br, d, J=9 Hz, 1 H), 1.6–1.9 (m, 2 H), 2.02 (br. d, J=9 Hz, 1 H), 2.79 (dd, J=9 and 10 Hz, 1 H), 3.22 (dd, J=1 and 10 Hz, 1 H), 3.91 (br. s, 1 H), 4.01 (dd, J=1 and 8 Hz, 1 H), 4.89 (s, 2 H), 5.65 and 5.88 (2 br. s, 1 H), 7.1–7.4 (m, 10 H).

Step 2: (2S,3S)-3-Benzyloxycarbonylamino-1-t-butoxycarbonyl-2-phenylpiperidine

To a solution of (2S,3S)-3-benzyloxycarbonylamino-2-phenylpiperidine (210 mg, 0.68 mmole) in methylene chloride (10 mL) at room temperature was added diisopropylethylamine (0.35 mL, 2.0 mmole) and di-t-butyl dicarbonate (221 mg, 1.0 mmole). The reaction was stirred for 16 hours and an additional aliquot of di-t-butyl dicarbonate (221 mg) was added. After stirring for another 2 days, the reaction was diluted with methylene chloride and quenched by addition of water. The mixture was separated and the aqueous was reextracted with 2 additional aliquots of methylene chloride. The organic layers were successively washed with a portion of brine, dried over sodium sulfate, combined and evaporated. The residue was purified by flash chromatography (50% ethyl acetate in hexanes) to afford 248 mg (90%) of the title compound. NMR (CDCl$_3$): δ 1.30 (s, 9 H), 1.5–1.8 (m, 2 H), 1.8–2.0 (m, 2 H), 3.15 (m, 1 H), 3.9–4.2 (m, 2 H), 4.32 (d, J=9 H), 5.05 (s, 2 H), 5.30 (m, 1 H), 7.2–7.4 (m, 10 H).

Step 3: (2S,3S)-3-Amino-1-t-butoxycarbonyl-2-phenylpiperidine

A solution of (2S,3S)-3-benzyloxycarbonylamino-1-t-butoxy-carbonyl-2-phenylpiperidine (240 mg, 0.59 mmole) in methanol (5 mL) was hydrogenated with 10% palladium on carbon (25 mg) under balloon pressure for 2 hours. The catalyst was removed by filtration and the solvent was evaporated to give 151 mg of title compound. This was used directly in the next step.

Step 4: (2S,3S)-1-t-Butoxycarbonyl-2-phenyl-3-[2-hydroxy-5-(5'-trifluoro-methyltetrazo-1-yl)phenylmethylene-amino]piperidine A solution of (2S,3S)-3-amino-1-t-butoxycarbonyl-2-phenylpiperidine (151 mg, 0.55 mmole), 2-hydroxy-5-(5'-trifluoro-methyltetrazo-1-yl)benzaldehyde (94 mg, 0.36 mmole) (prepared as described in Example 1) and acetic acid (0.034 mL, 0.58 mmole) in dichloroethane (4 mL) was stirred at room temperature for 5 minutes before sodium triacetoxyborohydride (154 mg, 0.73 mmole) was added. After stirring for 3 days, the reaction was poured into a saturated solution of sodium carbonate and was extracted with three portions of methylene chloride. The organic layers were successively washed with a portion of brine, dried over sodium sulfate, combined and evaporated. The residue was purified by flash chromatography (25% ethyl acetate in hexanes) to afford 165 mg (87%) of the title compound. NMR (CDCl$_3$): δ 1.35 (s, 9 H), 1.5–1.7 (m, 2 H), 1.7–1.9 (m, 1 H), 1.9–2.0 (m, 1 H), 2.0–2.2 (m, 1 H), 3.15 (m, 2 H), 3.9–4.2 (s and m, 3 H), 5.45 (br. s, 1 H), 6.96 (d, J=9 Hz, 1 H), 7.05 (d, J=2.5 Hz, 1 H), 7.21 (dd, J=2.5 and 9 Hz), 7.25–7.4 (m, 3 H), 7.45 (d, J=7 Hz, 2 H).

EXAMPLE 3

[2-Fluoromethoxy-5-(5-trifluoromethyl-tetrazol-1-yl)-benzyl]-([2S,3S]-2-phenyl-piperidin-3-yl)-amine The title compound is prepared essentially as outlined below.

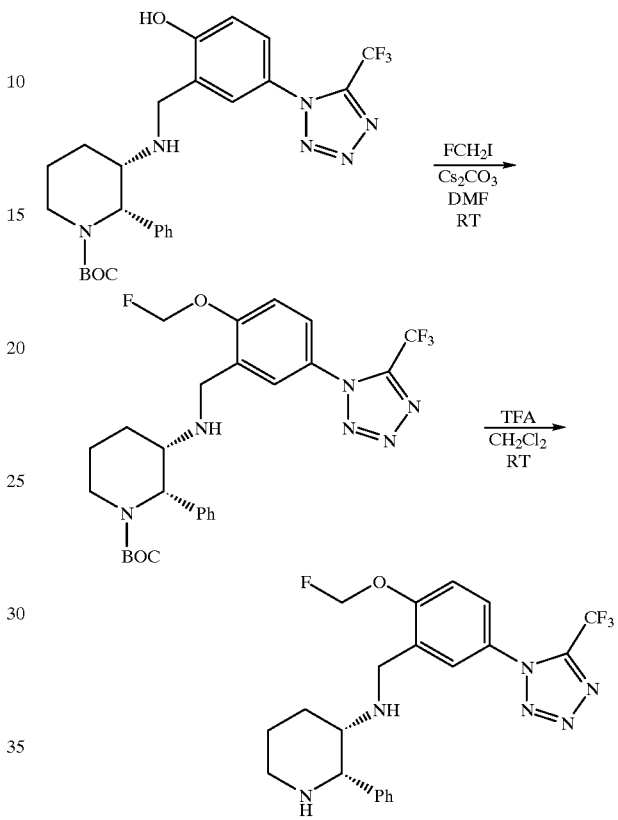

Step 1: [2-Fluoromethoxy-5-(5-trifluoromethyl-tetrazol-1-yl)-benzyl]-([2S,3S]-1-t-butoxy carbonyl-2-phenyl-piperidin-3-yl)-amine A room temperature solution of (2S,3S)-1-t-Butoxycarbonyl-2-phenyl-3-[2-hydroxy-5-(5'-trifluoro-methyltetrazo-1-yl)phenyl-methylene-amino]piperidine (100 mg, 0.19 mmol) in DMF (6.6 mL) was treated with Cs$_2$CO$_3$ (313 mg, 0.96 mmol) giving a yellow mixture. After stirring for several minutes at room temperature a solution of fluoromethyl iodide (0.09 mL) in DMF (1.2 mL) was added discharging the yellow color. After stirring at room temperature for 30 minutes, HPLC analysis (C18 Vydac protein and peptide column, 4.6×250 mm, 1 mL/min, linear gradient of 10% MeCN:H$_2$O (0.1% TFA) to 95% MeCN over 15 minutes, hold at 95% MeCN for 10 minutes, 254 nm) shows the title compound at 16.5 minutes. The reaction was diluted with H$_2$O/brine/aq. sat'd NH$_4$Cl and placed in a separatory funnel. The aqueous layer was extracted with ethyl acetate and the organic layers were combined, dried (MgSO$_4$), filtered and concentrated in vacuo to give 113 mg of crude product.

Step 2: [2-Fluoromethoxy-5-(5-trifluoromethyl-tetrazol-1-yl)-benzyl]-([2S,3S]-2-phenyl-piperidin-3-yl)-amine dihydrochloride.

A room temperature solution of [2-fluoromethoxy-5-(5-trifluoromethyl-tetrazol-1-yl)-benzyl]-([2S,3S]-1-t-butoxy carbonyl-2-phenyl-piperidin-3-yl)-amine (113 mg, 0.205 mmol) in methylene chloride (5 mL) was treated with trifluoroacetic acid (2.5 mL) and stirred at room temperature for 50 minutes. HPLC analysis (C18 Vydac protein and peptide column, 4.6×250 mm, 1 mL/min, linear gradient of 10% MeCN:H$_2$O (0.1% TFA) to 95% MeCN over 15 minutes, hold at 95% MeCN for 10 minutes, 254 nm) shows the title compound at 13.5 minutes. The reaction was concentrated in vacuo to give a yellow oil and transferred to a separatory funnel using ethyl acetate/aq. satd'd NaHCO$_3$. The layers were separated and the aqueous layer was extracted with ethyl acetate. The organic layers were combined, dried (MgSO$_4$), filtered and concentrated in vacuo to give 136 mg of crude title compound as a yellow oil. TLC (5:93:2 methanol:ethyl acetate:triethylamine) shows the title compound at 0.35 R$_f$. This material was dissolved in chloroform and purified by radial chromatography (5:93:2 methanol:ethyl acetate:triethylamine) to give 41.2 mg of pure product along with 50 mg of product containing small amounts of the corresponding phenol. The pure product was dissolved in diethyl ether, cooled to 0° C. and HCl (g) was bubbled into the ether. Removal of the ether and drying gave 48 mg of the hydrochloride salt as an off white solid.

EXAMPLE 4

[2-Fluoromethoxy-5-(5-trifluoromethyl-tetrazol-1-yl)-benzyl]-([2S,3S]-2-phenyl-piperidin-3-yl)-amine dihydrochloride The title compound is prepared essentially as outlined below.

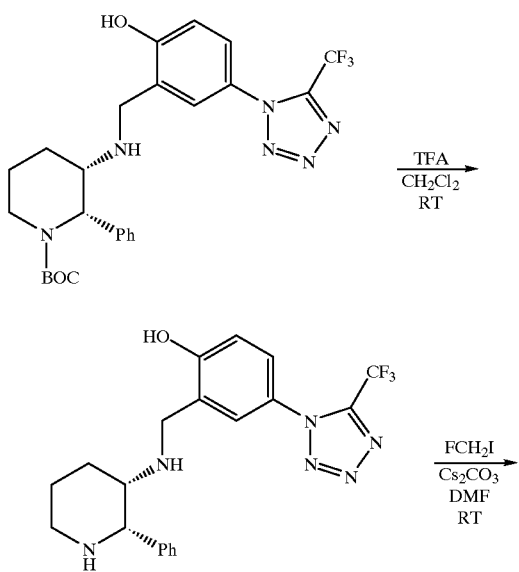

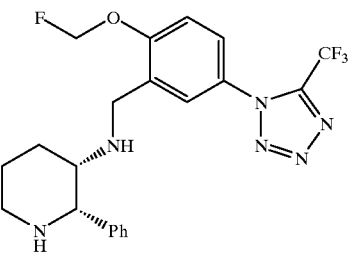

Step 1: [2-Hydroxy-5-(5-trifluoromethyl-tetrazol-1-yl)-benzyl]-([2S,3S]-2-phenyl-piperidin-3-yl)-amine dihydrochloride A room temperature solution of (2S,3S)-1-t-butoxycarbonyl-2-phenyl-3-[2-hydroxy-5-(5'-trifluoromethyltetrazo-1-yl)phenylmethylene-amino]piperidine (21 mg, 0.04 mmol) in methylene chloride (1 mL) was treated with trifluoroacetic acid (0.5 mL) and stirred at room temperature for 2 hours. The reaction was concentrated in vacuo and placed in a separatory funnel along with ethyl acetate/aq. sat'd NaHCO$_3$. The aqueous layer was extracted with ethyl acetate and the organic layers were combined, dried (MgSO$_4$), filtered and concentrated in vacuo to give 18.2 mg of the title compound as a yellow oil. This was dissolved in diethyl ether, cooled to 0° C. and HCl (g) was bubbled into the ether for about one minute. The ether was removed in vacuo and the residue was dried to give 20 mg of the product hydrochloride salt as a white solid.

Step 2: [2-Fluoromethoxy-5-(5-trifluoromethyl-tetrazol-1-yl)-benzyl]-([2S,3S]-2-phenyl-piperidin-3-yl)-amine dihydrochloride A room temperature solution of (2S,3S)-1-t-butoxycarbonyl-2-phenyl-3-[2-hydroxy-5-(5'-trifluoromethyltetrazo-1-yl)phenylmethylene-amino]piperidine (0.3 mg) in methylene chloride (0.1 mL) was treated with trifluoroacetic acid (0.1 mL) and stirred at room temperature for twenty minutes. HPLC analysis (C18 Vydac protein and peptide column, 4.6×250 mm, 1 mL/min, linear gradient of 10% MeCN:H$_2$O (0.1% TFA) to 95% MeCN over 20 minutes, 254 nm) shows disappearance of the starting material (17.5 minute retention time) with formation of the title compound (13 minute retention time). The reaction mixture was concentrated in vacuo. The residue was treated with DMF (0.05 mL), several milligrams of Cs$_2$CO$_3$ so a yellow color persisted and fluoromethyl iodide (1 uL). After stirring two hours at room temperature, HPLC analysis (C18 Vydac protein and peptide column, 4.6×250 mm, 1 mL/min, linear gradient of 10% MeCN:H$_2$O(0.1% TFA) to 95% MeCN over 15 minutes, hold at 95% MeCN for 10 minutes, 254 nm) shows the formation of the title compound (15 minute retention time) as determined by coinjection with an authentic standard.

EXAMPLE 5

[2-Fluoromethoxy-5-(5-methyl-tetrazol-1-yl)-benzyl]-([2S,3S]-2-phenyl-piperidin-3-yl)-amine hydrochloride The title compound is prepared essentially as outlined below.

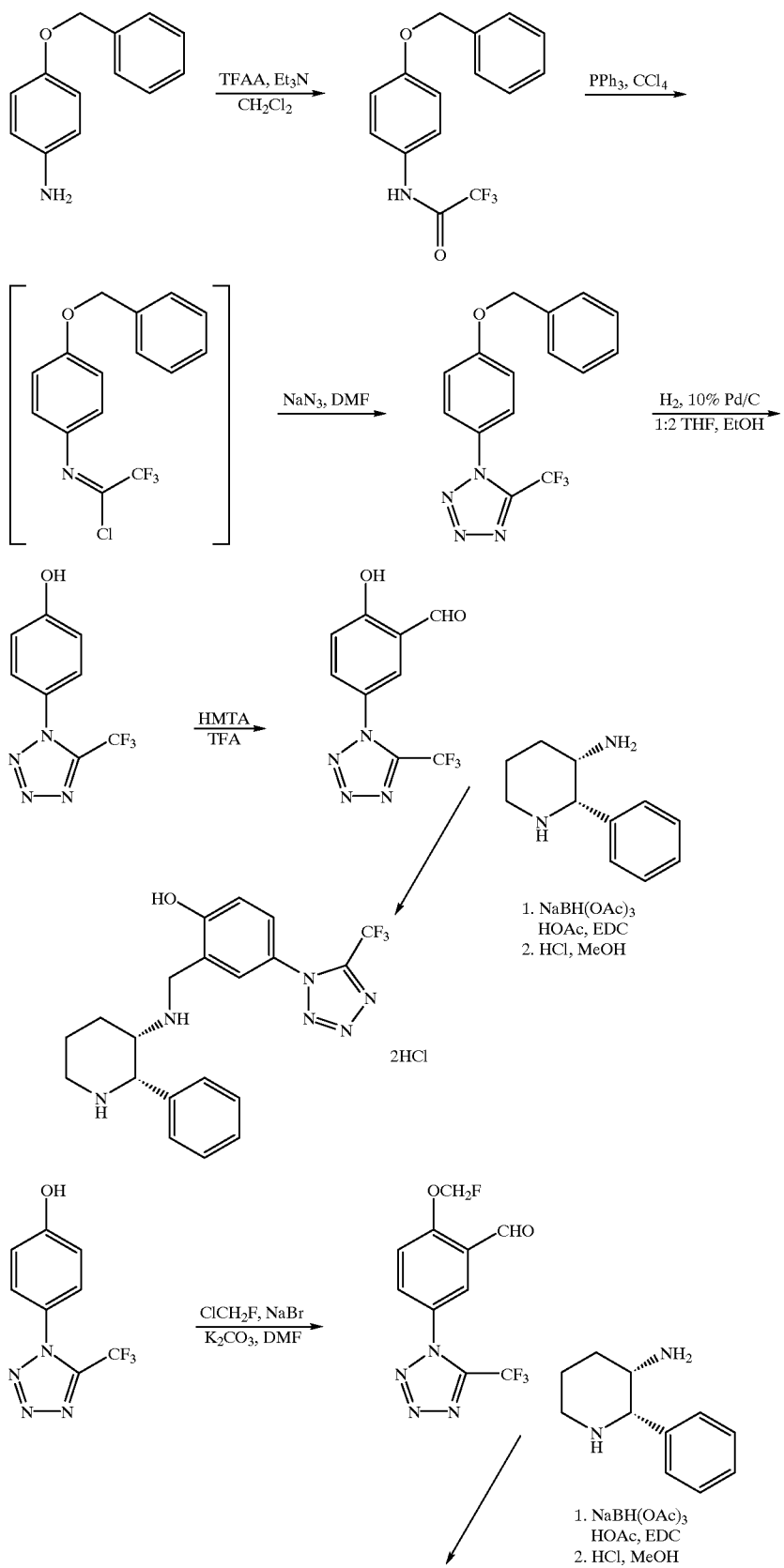

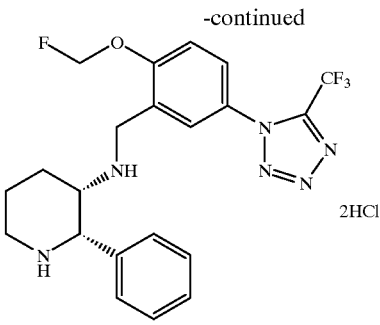

·2HCl

Step 1: N-(4-Benzyloxyphenyl)-2,2,2-trifluoroacetamide

A nitrogen purged 5 L round bottom flask fitted with an addition funnel, a mechanical stirrer and a nitrogen inlet was charged with 187.1 g (0.80 mol) of 4-benzyloxyaniline hydrochloride and methylene chloride (3L). The suspension was cooled to 5° C. and trifluoroacetic anhydride (115.5 mL, 171.7 g, 0.82 mol, 1.03 equiv) was added over 10 min. The suspension thickened (yellow-pink) with no measureable increase in temperature. Triethylamine (250 mL, 181.5 g, 1.79 mol, 2.25 equiv) was added over 20 min, during which time the temperature rose to 15° C. The ice bath was allowed to melt and the reaction warmed to room temperature with stirring overnight. The clear red solution was poured into 5 L of tert-butyl methyl ether, and washed with 2N HCl (1L), and brine (1 L). The solution was dried with magnesium sulfate, filtered, and concentrated affording the title compound as a thick paste. The compound was difficult to dry completely, therefore, a small sample was dried for characterization, and the bulk used as is in the next reaction: $^1$H NMR (CDCl$_3$) δ 5.05 (s, 2H), 7.0 (d, J=9 Hz, 2H), 7.08 (bs, 1H), 7.3–7.5 (m, 7H). MS (PB-EI) m/z 295. Anal. Calcd for C$_{15}$H$_{12}$F$_3$NO$_2$: C, 61.02; H, 4.10; F, 19.30; N, 4.74. Found: C, 60.89; H, 4.15; F, 19.04; N, 4.74.

Step 2: 4-Benzyloxyphenyl)-(1-chloro-2,2,2-trifluoroethylidene)-amine

Crude N-(4-benzyloxyphenyl)-2,2,2-trifluoroacetamide (theoretically 233 g, 0.80 mol of N-(4-benzyloxyphenyl)-2,2,2-trifluoro-acetamide was charged along with 2.5 L of carbon tetrachloride to a 5 L round bottom flask fitted with a distillation head, a condenser, a mechanical stirrer and a nitrogen inlet. The solvent was distilled until the temperature of the distillate reached 70° C. Triphenylphosphine (300 g, 1.15 mol, 1.44 equiv) was charged and the reaction refluxed overnight (12 h). TLC (25% CH$_2$Cl$_2$/Hex) and NMR indicated significant amounts of starting material remained. An additional 300 g of triphenyl-phosphine was added over several hours. After an additional 3.5 h the reaction was deemed complete by TLC (1:3 CH$_2$Cl$_2$:hexanes) and NMR (aromatic doublet shifts from δ 7.00 to 7.04, and the benzylic singlet shifts from δ 5.05 to 5.10). The reaction was cooled and refrigerated (0° C.) overnight. The thick suspension which resulted was filtered and the cake washed with 500 mL of carbon tetrachloride. A check of the cake indicated little to no product remained. The filtrate was concentrated affording the title compound as an oil which was used in the next reaction without purification: $^1$H NMR (CDCl$_3$) δ 5.1 (s, 2H), 7.04 (d, J=9 Hz, 2H), 7.0 7.26–7.73 (m,).

Step 3: 1-(4-Benzyloxyphenyl)-5-trifluoromethyl-1H-tetrazole

Crude 4-benzyloxy-phenyl)-(1-chloro-2,2,2-trifluoroethylidene)-amine from above (theoretically 251 g, 0.80 mol) was dissolved in DMF (1 L) in a nitrogen flushed 3L round bottom flask to which was added 100 g (1.54 mol, 1.93 equiv) of sodium azide. The reaction immediately started to get warm and was cooled with an ice-water bath. After 15 min the temperature leveled off at 33° C. When the temperature dropped to 25° C., the cooling bath was removed and the reaction stirred at ambient temperature overnight. Although the reaction was complete after 1.5 h, it was aged overnight as a matter of convenience. The reaction was diluted with 3.5 L of water and extracted with ether (1×1.5 L, 2×1 L) then ethyl acetate (1 L). The combined extracts were then washed with water (3×500 mL) and brine (500 mL), dried with magnesium sulfate, filtered and the filtrate concentrated to a dark redish-orange paste (432 g). This was dissolved in 2 L of methylene chloride and chromatographed (2 kg Silica Gel 60, 70–230 mesh, methylene chloride). The product containing fractions were concentrated to a paste. The paste was suspended in ether (1 L) and hexanes (1.5 L) were added. The product was collected by filtration and washed with hexanes. After drying, 196.9 g of white crytalline 1-(4-benzyloxyphenyl)-5-trifluoromethyl-1H-tetrazole was obtained (77.1% overall yield from starting 4-benzyloxyaniline hydrochloride): $^1$H NMR (CDCl$_3$) δ 5.14 (s, 2H), 7.13 (m, 2H), 7.33–7.45 (m, 7H). MS (PB-EI) m/z 320. Anal. Calcd for C$_{15}$H$_{11}$F$_3$N$_4$O: C, 56.25; H, 3.46; F, 17.80; N, 17.49. Found: C, 56.16; H, 3.56; F, 17.89; N, 17.45. KF <0.1%.

Step 4: 4-(5-Trifluoromethyl-tetrazol-1-yl)-phenol

A solution of 129 g (0.40 mol) of 1-(4-benzyloxyphenyl)-5-trifluoromethyl-1H-tetrazole in 900 mL 1:2 THF/ethanol was hydrogenated at ambient temperature over 6 g 10% Pd/C at 45 psi hydrogen for 12 h. The catalyst was removed by filtration through Celite®, the cake washed with ethanol, and the filtrate concentrated. The product was dissolved in ether, filtered through magnesium sulfate and concentrated. During concentration the product began to crystallize, as the product crystallized the mixture was flushed with hexanes to remove the ether. The resulting slurry was cooled to 0° C., aged 1 hr, filtered, and the cake washed with hexanes. The yield upon drying was 84.8 g (91.5%) of white crystalline 4-(5-trifluoromethyl-tetrazol-1-yl)-phenol: $^1$H NMR (CDCl$_3$) δ 5.6 (s, 1H), 7.07 (m, 2H), 7.35 (m, 2H). MS (EI) m/z 230. Anal. Calcd for C$_8$H$_5$F$_3$N$_4$O: C, 41.75; H, 2.19; F, 24.76; N, 24.34. Found: C, 41.76; H, 2.23; F, 24.53; N, 24.42. KF <0.1%.

Step 5: 2-Hydroxy-5-(5-trifluoromethyl-tetrazol-1-yl)-benzaldehyde

To a 2 L nitrogen purged round bottom flask fitted with a condenser was charged 67.7 g (0.29 mol) of 4-(5-trifluoromethyl-tetrazol-1-yl)-phenol, 540 mL trifluoroacetic acid, and 86.3 g (0.62 mol, 2.1 eq) of hexamethylenetetramine. The solution was heated to reflux and refluxed for 4 h. An additional 10 g (0.07 mol, 0.24 equiv) of hexamethylenetetramine was added and the solution refluxed overnight. The reaction was cooled and poured slowly into 3 L of 1N H$_2$SO$_4$. The suspension was diluted with an additional 500 mL of water and aged at room temperature for 30 min and at 0° C. and for additional 30 min. The yellow suspension was filtered and the cake washed with water until the filtrate was neutral. The cake was dissolved in methylene chloride and filtered through 300 g of Silica Gel 60 (70–230 mesh) and flushed with 6 L of methylene chloride. The solvent was removed in vacuo and the residue flushed with hexanes. The resulting slurry was cooled to room temperature and filtered. The white crystalline product that was obtained was dried yielding 50.4 g (66.4% yield) of the title compound. An additional 6.9 g (9.1%, for a combined yield of 57.3 g, 75.5% yield) was obtained by extracting the aqueous filtrate with ether and chromatographing (Silica Gel 60, methylene chloride): $^1$H NMR (CDCl$_3$) δ 7.23 (d, J=9 Hz, 1H), 7.62 (dd, J=9, 2 Hz, 1H), 7.73 (d, J=2.5 Hz, 1H), 9.96 (s, 1H). MS (EI) m/z 258. Anal. Calcd for C$_9$H$_5$F$_3$N$_4$O$_2$: C, 41.87; H, 1.95; F, 22.08; N, 21.70. Found: C, 41.87; H, 1.98; F, 22.61; N, 21.74.

Step 6: 2-Fluoromethoxy-5-(5-trifluoromethyl-tetrazol-1-yl)-benzaldehyde

A 500 mL nitrogen purged round bottom flask fitted with a dry-ice condenser was cooled to −78° C. and 50 mL (ca. 40 g by cylinder difference) of chlorofluoromethane was condensed. DMF (200 mL), 2-hydroxy-5-(5-trifluoromethyl-tetrazol-1-yl)-benzaldehyde (40 g, 0.155 mol), powdered potassium carbonate (22 g, 0.159 mol, 1.03 equiv) and sodium bromide (22 g, 0.21 mol) were carefully added. An additional 100 mL of DMF was added and the dry-ice bath was removed. The pale yellow suspension was warmed first to room temperature, then to 70–75° C. (oil bath). Gentle reflux was noted. After 3 h, an additional 30 g of NaBr was added. The condenser was kept cold for ca. 10 h and allowed to warm to room temperature overnight. The white suspension which resulted was diluted with 2 L of water and extracted with ether (1×1 L, 2×500 mL). The combined extracts were washed with water (4×250 mL) and brine (500 mL), dried with magnesium sulfate, filtered and the filtrate concentrated. During concentration the product began to crystallize. The filtrare was concentrated to a small volume and the mixture flushed with hexanes. The resulting slurry was cooled to 0° C., aged 1 hr, filtered, and the cake washed with hexanes. The yield upon drying was 42.2 g (93.8%) of white crystalline 2-fluoromethoxy-5-(5-trifluoromethyl-tetrazol-1-yl)-benzaldehyde: $^1$H NMR (CDCl$_3$) δ 5.91 (d, J$_{H-F}$=30.5 Hz, 2H), 7.47 (d, J=9 Hz, 1H), 7.72 (dd, J=9, 2.7 Hz, 1H), 8.02 (d, J=2.7 Hz, 1H), 10.49 (s, 1H). MS (EI) m/z 290. Anal. Calcd for C$_{10}$H$_6$F$_4$N$_4$O$_2$: C, 41.39; H, 2.08; F, 26.19; N, 19.31. Found: C, 41.39; H, 1.98; F, 25.79; N, 19.53.

Step 7: [2-hydroxy-5-(5-methyl-tetrazol-1-yl)-benzyl]-([2S,3S]-2-phenyl-piperidin-3-yl)-amine hydrochloride

[2S]-Phenyl-piperidin-[3S]-yl-amine[2R,3R]-bis(4-methyl-benzyloxy)-succinate (5 g, 8.33 mmol)) was partitioned between 100 mL of methylene chloride and 25 mL of 1N NaOH. The aqueous was re-extracted with 50 mL of methylene chloride and the combined organic layer dried with sodium sulfate, filtered and concentrated. The colorless oil was dissolved in 200 mL of 1,2-dichloroethane and 2.4 g (9.3 mmol, 1.12 equiv) of 2-hydroxy-5-(5-methyl-tetrazol-1-yl)-benzaldehyde, 3.75 g (17.7 mmol, 2.1 equiv) of sodium triacetoxyborohydride and 24 drops of glacial acetic acid were added. The mixture was stirred at room temperature under nitrogen for 16 h, during which time the reaction changed from cloudy yellow to white. The reaction was diluted with methylene chloride and washed with 50% saturated sodium bicarbonate solution. The aqueous was extracted with methylene chloride and the combined extracts dried with sodium sulfate, filtered and concentrated. The residue was dissolved in ether (100 mL) and extracted with 1N HCl (2×100 mL). The combined aqueous layer was extracted with ether, made basic with 5N NaOH (50 mL), and extracted with methylene chloride (2×200 mL). The combined methylene chloride extracts were dried with sodium sulfate and flash chromatographed (600 g Silica Gel 60, 230–400 mesh, 98:2 methylene chloride/methanol). The product containing fractions were concentrated and the residue dissolved in of methanol (50 mL). HCl (1 mL 12 N) was added and the solution concentrated to ca. 25 mL. Ether (200 mL) was added and the resulting white suspension cooled to 0° C. and aged for 30 min. The product was collected by filtration and dried (60° C. in vacuo) affording 2.17 g of the title compound as a white crytalline solid: $^1$H NMR (CD$_3$OD) δ 1.95–2.05 (m, 1H), 2.20–2.35 (m, 1H), 2.40–2.55 (m, 2H), 3.25–3.35 (m, 1H), 3.66 (dt, J=12, 3.4 Hz, 1H), 3.88 (d, J=13.4 Hz, 1H), 4.16 (bs, 1H), 4.17 (d, J=13.4 Hz, 1H), 4.89 (HOD), 5.01 (bs, 1H), 6.99 (d, J=8.8 Hz, 1H), 7.42 (d, J=2.6 Hz, 1H), 7.45–7.60 (m, 4H), 7.70 (d, J=6.3 Hz, 2H). MS (ESI) m/z 419 (m−HCl$_2$).

Step 7: [2-Fluoromethoxy-5-(5-methyl-tetrazol-1-yl)-benzyl]-([2S,3S]-2-phenyl-piperidin-3-yl)-amine hydrochloride

[2S]-Phenyl-piperidin-[3S]-yl-amine[2R,3R]-bis(4-methyl-benzyloxy)-succinate (7.5 g, 12.5 mmol) was partitioned between 150 mL of methylene chloride and 50 mL of 1N NaOH. The aqueous was re-extracted with 100 mL of methylene chloride and the combined organic layer dried with sodium sulfate, filtered and concentrated. The colorless oil was dissolved in 250 mL of 1,2-dichloroethane and 3.93 g (13.5 mmol) of 2-fluoromethoxy-5-(5-methyl-tetrazol-1-yl)-benzaldehyde, 5.63 g (26.6 mmol) of sodium triacetoxyborohydride and 36 drops of acetic acid were added. The mixture was stirred at room temperature under nitrogen for 16 h, during which time the reaction remained cloudy white. The reaction was diluted with methylene chloride and washed with 50% saturated sodium bicarbonate solution. The aqueous was extracted with methylene chloride and the combined extracts dried with sodium sulfate, filtered and concentrated. The residue was flash chromatographed (600 g Silica Gel 60, 230–400 mesh, 97.5:2.5 methylene chloride/methanol). The product containing fractions were concentrated and the residue dissolved in ethanol (125 mL). HCl (2 mL 12 N) was added and the solution concentrated to ca 60 mL. Ether (400 mL) was added and the resulting white suspension aged at room temperature for 20 min, then cooled to 0° C. and aged for 30 min. The product was collected by filtration and dried (60° C. in vacuo) affording 4.87 g of the title compound as a white crytalline solid: Chloride titration: 13.8% (theory 13.6%); KF: 0.05%; TG: 0.1%; Purity: 99.8% (based on HPLC area-%). Impurity profile (area-%): total impurities 0.2%; RRT 1.11 (unknown) 0.1%; 2 others, each <0.10%; no others >0.05%. [Precursor found to be one of the impurities <0.10% (RRT 0.69, ave,. 0.08%). $^1$H NMR (C D$_3$OD) δ 1.94–2.05 (dt, J=14.3, 3.2 Hz, 1H), 2.25–2.55 (m, 3H), 3.29–3.37 (m, 1H), 3.68 (d, J=12.8 Hz, 1H), 3.76 (d, J=13.3 Hz, 1H), 4.14 (bs, 1H), 4.21 (d, J=13.3 Hz, 1H), 4.89 (HOD), 5.05 (bs, 1H), 5.87 (dq, J$_{H-F}$=53.2, J$_{H-H}$=2.8, 3.4 Hz, 2H), 7.44 (d, J=8.7 Hz, 1H), 7.50–7.59 (m, 3H), 7.66 (d, J=2.5 Hz, 1 H). 7.71–7.76 (m, 3H), MS (ESI) m/z 451 (m+1).

EXAMPLE 6

[$^{18}$F] [2-Fluoromethoxy-5-(5-methyl-tetrazol-1-yl)-benzyl]-([2S,3S]-2-phenyl-piperidin-3-yl)-amine The title compound is prepared essentially as described in Example 3 and as outlined below. The labeling was done utilizing $^{18}$F-labeled iodofluoromethane or $^{18}$F-labeled bromofluoromethane as the labeling precursor and the Boc protected intermediate ((2S,3S)-1-t-butoxy-carbonyl-2-phenyl-3-[2-hydroxy-5-(5'-trifluoro-methyltetrazo-1-yl)phenyl-methylene-amino]piperidine) as the unlabeled precursor.

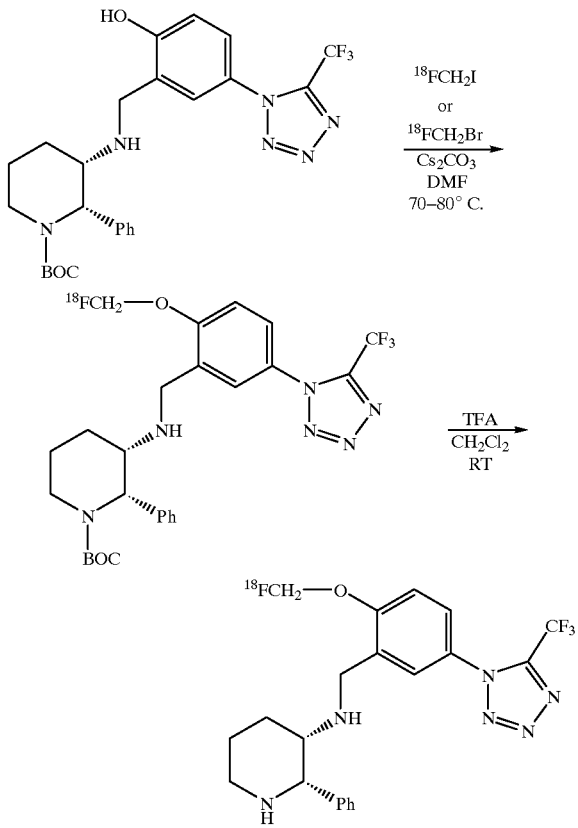

Step 1: Radionuclide production ([$^{18}$F]fluoride)

$^{18}$F⁻ is obtained via the nuclear reaction: $^{18}$O(p,n)$^{18}$F. This is achieved by bombarding a silver target containing $^{18}$O enriched water with accelerated protons (17 MeV). A Cyklotron (Scanditronix MC17 cyclotron) and systems for the production of primary labelled precursor are used for the radionuclide production.

Step 2: Removal of water from $^{18}$F⁻

The target water is removed by 3–5 azeotropic distillations with acetonitrile (around 5×1 ml) at 105° C. in the presence of a phase transfer catalyst (e.g. kryptofix-2.2.2.) and a suitable counterion (K⁺).

Step 3: Synthesis of [$^{18}$F]fluorobromomethane

The labelling precursor [$^{18}$F]FCH$_2$Br is synthesized from dibromomethane via a nucleophilic substitution reaction, using a phase transfer catalyst (Kryptofix-2.2.2). The residue obtained after removal of the target water is taken up in acetonitrile and added to CH$_2$Br$_2$. The reaction mixture is heated at around 60° C. and the product is transferred by a stream of helium through a preparative GC-column (10×250 mm, Porapak Q, 50/80 mesh) heated at around 100° C. to separate [$^{18}$F]FCH$_2$Br from the solvents and the other reagents.

Step 4: [$^{18}$F] [2-Fluoromethoxy-5-(5-methyl-tetrazol-1-yl)-benzyl]-([2S,3S]-2-phenyl-piperidin-3-yl)-amine Purified CH$_2$Br[$^{18}$F]F is trapped in dimethylformamide, containing 0.7–1.3 mg of (2S,3S)-1-t-butoxycarbonyl-2-phenyl-3-[2-hydroxy-5-(5'-trifluoro-methyltetrazo-1-yl) phenylmethylene-amino]-piperidine) and approximately 1 mg of cesium carbonate (Cs$_2$CO$_3$). The alkylation reaction is performed at 70–80° C. for approximately 10 min to promote the fluoromethyl alkylation of the O-desfluoromethyl precursor. A helium flow is applied and the solvent removed. The reaction mixture is then allowed to cool down and 75–125 ml of trifluoroacetic acid is added and the BOC group removed. Sterile water is added and the solution injected onto a semi-preparative HPLC column (eg. LC-C18 250×10 mm). The collected fraction is transferred to a rotary evaporator for removal of the HPLC mobile phase. To the residue is added approximately 5 ml of a solution of sterile 5% aqueous dextrose containing 1% of ethanol and sterile phosphate buffer (approximately 250 ul, 0.1 M pH 7.4). The solution is filtered through a sterilised 0.2 mm filter into a sterilized injection vial. A sample is taken for determination of radiochemical and chemical purity and pH. The radioactivity is measured using a well-counter. The radiolabeled product is delivered dissolved in approximately 5 ml of sterile 5% aqueous dextrose solution containing 1% ethanol adjusted to pH 6.8–7.6 with around 250 ul of 0.1 M phosphate buffer pH 7.4. The solution is sterile filtered. The radiolabeled product is radiochemically pure (>90%).

EXAMPLE 7

Preclinical Biodistribution of [$^{18}$F][2-Fluoromethoxy-5-(5-trifluoromethyl-tetrazol-1-yl)-benzyl]-([2S,3S]-2-phenyl-piperidin-3-yl)-amine To determine the distribution of [$^3$H] [2-fluoromethoxy-5-(5-trifluoromethyl-tetrazol-1-yl)-benzyl]-([2S,3S]-2-phenyl-piperidin-3-yl)-amine in guinea pig and gerbil brains, 2–5 μCi of radiotracer (in water) was injected via catheterized jugular vein under ketamine/xylazine anesthesia. To determine the extent of specific binding of [$^3$H][2-fluoromethoxy-5-(5-trifluoromethyl-tetrazol-1-yl)-benzyl]-([2S,3S]-2-phenyl-piperidin-3-yl)-amine, a potent, selective neurokinin-1 receptor antagonist was injected (1 mpk) 5 min. prior to injection of the radiotracer. Two animals were used for each data point obtained in the in vivo studies. Animals were euthanized 60 min. after injection of radiotracer and brains removed. Frontal cortex, caudate/putamen and cerebellum were dissected, weighed, and solubilized in Biosolv. Excess base was neutralized, scintillation cocktail added, samples dark adapted and counted in a scintillation counter. Data are expressed as %-injected dose/g wet weight tissue.

Similarly, to determine the distribution of [$^{18}$F][2-fluoromethoxy-5-(5-trifluoromethyl-tetrazol-1-yl)-benzyl]-([2S,3S]-2-phenyl-piperidin-3-yl)-amine in guinea pig brain, radiotracer (in water) was injected via catheterized jugular vein under ketamine/xylazine anesthesia. To determine the extent of specific binding of [$^{18}$F][2-fluoromethoxy-5-(5-trifluoromethyl-tetrazol-1-yl)-benzyl]-([2S,3S]-2-phenyl-piperidin-3-yl)-amine, a potent, selective neurokinin-1 receptor antagonist was injected (1 mpk) 5 min. prior to injection of the radiotracer. The biopsy data were obtained from two animals for each condition. Autoradiography was obtained from one guinea pig. Animals were euthanized 180 min. after injection of radiotracer and brains removed. Frontal cortex, caudate/putamen and cerebellum were dissected, weighed and counted in a scintillation counter. Data are expressed as %-injected dose/g wet weight tissue.

The regional cerebral distribution and uptake of the labeled tracer was studied utilizing a digital autoradiographic technique (Fuji BAS 5000). This technique has the advantages of being very sensitive towards detecting the β+ particles emitted in the decay of $^{18}F$ as well as having comparatively good spatial resolution (pixel size 25×25 μm). After sacrifice the brains were removed, chilled in isopentane/$CO_2$-ice to approximately −20° C. and sectioned on a cryomicrotome. The thickness of the cuts were set at 20 μm. These were set on glass microscope slides and put into a light tight box. The radiation sensitive imaging phosphor was placed inside the box such that it covered all slides. After a four hour exposure time (two half-lives for $^{18}F$) the phosphor was removed and scanned for the stored image. The scan files were stored on Jazz discs (Iomega Inc.). The files were analyzed for uptake of radioactivity in frontal caudate putamen, cortex, some thalamic structures as well as cerebellum with the TINA program supplied by the manufacturer of the phosphoimaging device. An absolute calibration for the activity per area unit in the images was determined by measuring separately the uptake in cerebellum for each animal, as described in the previous sections. From these analyses the ratios of uptake between the various areas as well as absolute uptakes could be determined The distribution of [$^{18}F$][2-fluoromethoxy-5-(5-trifluoro-methyl-tetrazol-1-yl)-benzyl]-([2S,3S]-2-phenyl-piperidin-3-yl)-amine was determined in guinea pig. At 180 min. post-injection of radiotracer, a receptor-specific signal was observed in the caudate/putamen which was similar to that obtained with [$^{3}H$][2-fluoromethoxy-5-(5-trifluoro-methyl-tetrazol-1-yl)-benzyl]-([2S,3S]-2-phenyl-piperidin-3-yl)-amine. There was little difference in the specific signal obtained at 60 min. and 180 min. The autoradiography shows binding in a number of structures in the guinea pig brain, all of which are known to have neurokinin-1 receptors present. Very low levels of radioactivity was observed in regions which do not have significant neurokinin-1 receptor concentrations.

Quantitative analysis of the autoradiographs to obtain % dose/g values (a measure of specific binding in this case since non-specific binding is negligible with this tracer) for several regions, including caudate (0.24), cortex (0.084) and cerebellum (0.019) gave results that were in good agreement with those obtained by dissection.

The highest concentration of radioactivity was observed in lung, pancreas and intestines. It is interesting to note that a substantial specific signal was observed in both the pancreas and the intestines. In addition, only low levels of radioactivity were found in bone and skull which indicates that in vivo defluorination does not occur to any great extent since fluoride ion selectively accumulates in bone, and, in fact, [$^{18}F$]fluoride ion has been used as a diagnostic bone imaging agent In conclusion, [$^{3}H$][2-fluoromethoxy-5-(5-trifluoromethyl-tetrazol-1-yl)-benzyl]-([2S,3S]-2-phenyl-piperidin-3-yl)-amine and [$^{18}F$][2-fluoromethoxy-5-(5-trifluoromethyl-tetrazol-1-yl)-benzyl]-([2S,3S]-2-phenyl-piperidin-3-yl)-amine showed specific binding in vivo to the neurokinin-1 receptor in the caudate/putamen of guinea pigs and gerbils.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compound of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed:

1. A compound which is:

[$^{18}F$][2-fluoromethoxy-5-(5-trifluoromethyl-tetrazol-1-yl)-benzyl]-([2S,3S]-2-phenyl-piperidin-3-yl)-amine or a pharmaceutically acceptable salt thereof.

2. A radiopharmaceutical composition which comprises the compound of claim 1 and at least one pharmaceutically acceptable carrier or excipient.

3. A method for the diagnostic imaging of neurokinin-1 receptors in a mammal which comprises administering to a mammal in need of such diagnostic imaging an effective amount of the compound of claim 1, and obtaining an image of neurokinin-1 receptors using positron emission tomography.

4. The method of claim 3 wherein the mammal is a human.

5. A method for the diagnostic imaging of the brain in a mammal which comprises administering to a mammal in need of such diagnostic imaging an effective amount of the compound of claim 1, and obtaining an image of the brain using positron emission tomography.

6. The method of claim 5 wherein the mammal is a human.

7. A method for the diagnostic imaging of tissues bearing neurokinin-1 receptors in a mammal which comprises administering to a mammal in need of such diagnostic imaging an effective amount of the compound of claim 1, and obtaining an image of the tissues using positron emission tomography.

8. The method of claim 7 wherein the mammal is a human.

9. A method for the diagnostic imaging of substance P binding sites in tissues of a mammalian species which comprises administering to the mammalian species in need of such diagnostic imaging an effective amount of the compound of claim 1, and obtaining an image of the substance P binding sites using positron emission tomography.

10. The method of claim 9 wherein the mammal is a human.

11. A method for the detection or quantification of neurokinin-1 receptors in mammalian tissue which comprises contacting such mammal tissue in which such detection or quantification is desired with an effective amount of the compound of claim 1, and detecting or quantifyino the neurokinin-1 receptors using positron emission tomography.

12. The method of claim 11 wherein the mammalian tissue is human tissue.

13. A process for the preparation of [$^{18}F$][2-fluoromethoxy-5-(5-trifluoromethyl-tetrazol-1-yl)-benzyl]-([2S,3S]-2-phenyl-piperidin-3-yl)-amine which comprises:

contacting ((2S,3S)-1-t-butoxycarbonyl-2-phenyl-3-[2-hydroxy-5-(5'-trifluoro-methyltetrazo-1-yl) phenylmethylene-amino]piperidine) with an alkylating agent selected from: [$^{18}$F]iodofluoromethane and [$^{18}$F]bromofluoromethane in the presence of cesium carbonate in dimethylformamide at a temperature of about 70–80° C., followed by contacting the resultant product with trifluoracetic acid, to give [$^{18}$F][2-fluoromethoxy-5-(5-trifluoromethyl-tetrazol-1-yl)-benzyl]-([2S,3S]-2-phenyl-piperidin-3-yl)-amine.

14. The process of claim 13 wherein the alkylating agent is [$^{18}$F]bromofluoromethane.

* * * * *